(12) United States Patent
Fleischmann

(10) Patent No.: US 7,208,006 B2
(45) Date of Patent: Apr. 24, 2007

(54) PROCESS AND INSTRUMENT FOR STRETCHING TISSUE OF SKIN

(76) Inventor: Wilhelm Fleischmann, Wieselweg 26, 74321 Bietigheim-Bissingen (DE)

( * ) Notice: Subject to any disclaimer, the term of this patent is extended or adjusted under 35 U.S.C. 154(b) by 473 days.

(21) Appl. No.: 10/378,518

(22) Filed: Mar. 3, 2003

(65) Prior Publication Data
US 2003/0225436 A1 Dec. 4, 2003

(30) Foreign Application Priority Data
Mar. 1, 2002 (DE) ................................ 102 09 122

(51) Int. Cl.
*A61B 17/08* (2006.01)
(52) U.S. Cl. ....................... 606/216; 606/218
(58) Field of Classification Search ............... 606/213, 606/215, 216, 217, 218
See application file for complete search history.

(56) References Cited

U.S. PATENT DOCUMENTS

| | | | | |
|---|---|---|---|---|
| 5,127,412 A | * | 7/1992 | Cosmetto et al. ............ 128/898 |
| 5,234,462 A | * | 8/1993 | Pavletic ....................... 606/215 |
| 5,263,971 A | * | 11/1993 | Hirshowitz et al. .......... 606/216 |
| 5,441,540 A | * | 8/1995 | Kim ................................ 606/1 |
| 5,486,196 A | * | 1/1996 | Hirshowitz et al. .......... 606/218 |
| 5,507,775 A | * | 4/1996 | Ger et al. ..................... 606/216 |
| 5,549,640 A | | 8/1996 | Fontenot |
| 5,549,713 A | * | 8/1996 | Kim ............................. 606/131 |
| 5,618,310 A | | 4/1997 | Ger et al. |
| 5,662,714 A | * | 9/1997 | Charvin et al. .......... 623/15.12 |
| 5,723,009 A | * | 3/1998 | Frechet et al. ............... 128/898 |
| 5,759,193 A | * | 6/1998 | Burbank et al. ............. 606/213 |
| 5,814,067 A | | 9/1998 | Fleischmann |
| 6,120,525 A | * | 9/2000 | Westcott ...................... 606/216 |
| 6,254,624 B1 | | 7/2001 | Oddsen et al. |
| 6,733,537 B1 | * | 5/2004 | Fields et al. ................ 623/66.1 |

OTHER PUBLICATIONS

Hirshowitz, B et al: "Reconstruction of the tip of the nose and ala by load cycling of the nasal skin and harnessing of extra skin." In: Plast Reconstr Surg 1986; 76:316.
Melis P et al: "Primary Skin Closure of a Large Groin Defect After Inguinal Lymphadenectomy for Penile Cancer Using a Skin Stretching Device". In: The Journal of Urology 1998;159(1):185-187.

\* cited by examiner

*Primary Examiner*—Anhtuan T. Nguyen
*Assistant Examiner*—Darwin P. Erezo
(74) *Attorney, Agent, or Firm*—Akerman Senterfitt; Peter Chiabotti

(57) ABSTRACT

For stretching tissue of the skin a pull force is introduced into the skin via hooks (22) stuck into the skin at points. The hooks (22) are arranged adjacent to each other in a row transverse to the pull direction. Via the hooks (22) a high pull force can be introduced into the skin for a long stretch time. The high pull force is respectively alternatingly introduced via a portion of the hooks (22) while the other portion of the hooks (22) is relaxed. Thereby tissue necrosis on the pressure side of the hooks (22) is prevented even in the case of high pull forces and longer stretch durations.

10 Claims, 2 Drawing Sheets

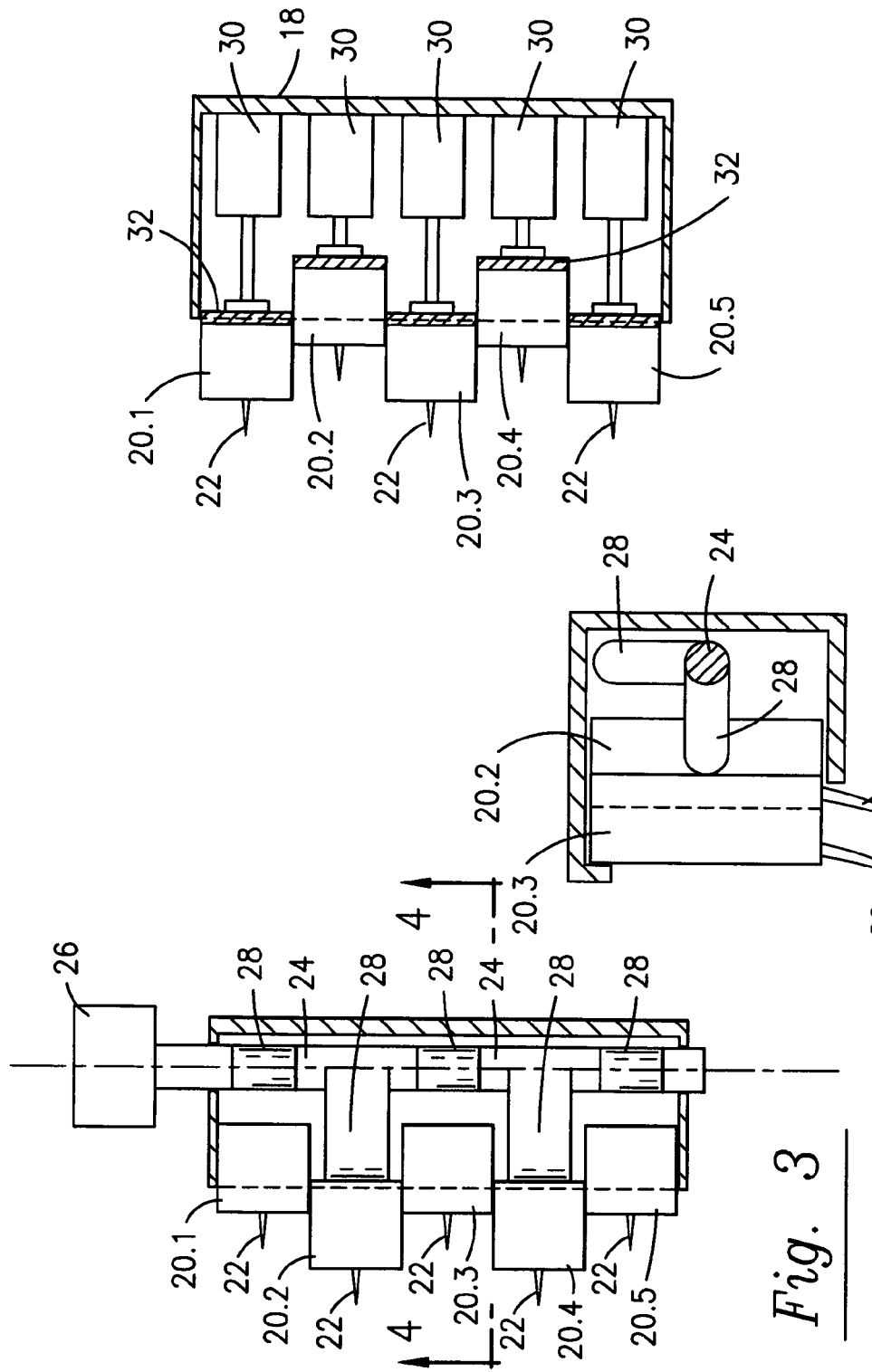

PROCESS AND INSTRUMENT FOR STRETCHING TISSUE OF SKIN

BACKGROUND OF THE INVENTION

1. Field of the Invention

The invention concerns a process and an instrument for stretching tissue of skin.

2. Description of the Related Art

For closing large wounds and skin defects it is known from, for example, U.S. Pat. No. 5,486,196 and U.S. Pat. No. 5,618,310 to mechanically stretch the skin surrounding the wound or the skin defect, thereby inducing an accelerated tissue regeneration. Distractors are employed for this skin stretching, which are anchored in the skin and include pulling means. These pulling means transmit a pulling force to the skin tissue for stretching the skin. A higher pull force brings about a stronger tissue proliferation. A high pull force however also has as a consequence that on the pressure side, ahead of the pull means, the skin tissue is compressed. In the instrument known from U.S. Pat. No. 5,486,196 the pull force is transmitted to the skin tissue via a long inter-dermal needle, which is anchored in the skin parallel to the edge of the wound. Thereby higher pull forces can be transmitted to skin tissue, without the pressure on the pressure side of the long needle rising above a critical closure pressure of the tissue system, which could lead to ischemia of the tissue. In the case of the instrument disclosed in U.S. Pat. No. 5,618,310 the pull force is introduced via a needle stuck into the skin at one point. Accordingly, the pull force is limited such that the critical closure pressure which could lead to ischemia on the pressure side of the needle is not exceeded. This limitation on the pull force also means a limitation on the stretching of the skin, so that an optimal tissue new formation is not achieved.

SUMMARY OF THE INVENTION

The invention is concerned with the task of providing a process and an instrument via which, for the stretching of the tissue of the skin, a high pull force can be introduced point wise into skin without the pull means causing damage of the tissue on the pressure side.

This task is inventively solved by a process with the features of claim 1 and by an instrument with the features of claim 8.

Preferred embodiments of the invention are disclosed in the respective dependent claims.

The essential idea of the invention is comprised therein, that a cyclic alternating pull force is introduced into the skin via the pull means anchored at a point in the skin. Therein the pull force preferably alternates, between two different values. The first value of the pull force is selected to be as large as possible, in order to stimulate a high as possible tissue new formation. This first value of the pull force is limited in its upper value essentially only by the resistance to tear of the skin. The first value is thus selected to be so high, that on the pressure side of the pull force the critical closure pressure of the venous capillary system of the skin is exceeded and thus ischemia is caused. This high pull force is maintained for a period of time which is within the ischemia tolerance duration of the skin tissue. Any duration of ischemia longer than this tolerance duration leads to a pressure induced dying of the skin tissue and therewith to a necrosis on the pressure side of the pull means. The ischemia tolerance duration of skin tissue is approximately 6 to 7 hours. Prior to reaching this ischemia tolerance duration, at which necrosis of the skin tissue is to be feared on the pressure side of the pull means, the pull force is reduced to a second value, which is so selected that the pressure exercised on the tissue on the pressure side of the pull means lies below the critical closure pressure of approximately 20–40 mm Hg. As a result of the pressure reduction the tissue is freed again ahead of the pull means for blood perfusion in the tissue and a rapid maximal reperfusion of the tissue occurs. This reperfusion occurs already after approximately 15 seconds, so that after approximately 0.5 to 5 minutes a complete perfusion and blood flow through the tissue on the pressure side of the pull means is ensured and the pull force can again be brought to the first high value. As a result of this cyclic change of the pull force a very high pull force for the tissue stretching of the skin can be employed for a prolonged duration of up to several days without the occurrence of a damaging of the skin and in particular a necrosis of the tissue on the pressure side of the pull means. The process and the instrument are thus suited in particular for the prolonged skin distraction for closure of large surface area skin defects.

In a preferred embodiment of the invention two groups of pull means are anchored in the skin, wherein the pull means of the two groups are arranged alternatingly side-by-side and preferably in a row transverse to the direction of the pull force. Via the first group of the pull means the first high pull force is introduced into the skin, during which time the second group of pull means is relaxed and introduces the second—lower—pull force. The two groups of pull means thereby alternate periodically over time in the value of their pull force, wherein the periodicity of the change-over is smaller than the ischemia tolerance of the skin tissue. Thereby continuously the maximal pull force is exercised upon the skin by one of the groups of the pull means, so that the optimal pull force for tissue regeneration is exercised without interruption. On the other hand, the pull force is respectively alternatingly relaxed, so that the tissue on the pressure side of the pull means can respectively regenerate completely during this relaxation phase.

In an advantageous design the pull means are in the form of hooks, which are stuck into the skin. In this case the hooks are in the form of hook modules in a hook receptacle, wherein the hook receptacle receives at least two hook modules, so that respectively at least one hook is available for each of the two groups. The hook modules in the hook receptacles are advanced preferably alternatingly by suitable adjusting means in the direction of the pull force. On the hook receptacles a high pull force with the first value is continuously exercised. This pull force is introduced into the skin via the hooks of the respective advanced hook module. The hooks of the respective non-advanced hook module is in this manner relaxed. The relaxed hook module is retracted by the elasticity of the skin until it no longer exercises any substantial pull force upon the skin. Alternatively the relaxed hook module can be pulled back by a spring force. It is likewise also possible to retract the relaxed hook module by positive control means.

The repositioning of the hook module, that is the advancing of the hook module exercising the pull force and the releasing or in the case may be the drawing back of the released hook module can occur in various ways. Since with regard to the ischemia tolerance duration of approximately 6 to 7 hours, it can be calculated that if the alternation between the two groups of pull means should be carried out in time intervals of several hours, a simple manual adjustment would be practicable. For an automated long duration treatment the adjustment can be carried out using an electric motor or a pneumatic means, which are adapted to be automatically controlled.

BRIEF DESCRIPTION OF THE DRAWING

In the following the invention will be described in greater detail on the basis of the illustrative embodiments represented in the figures. There is shown FIG. 1 a side view of an instrument according to the invention, FIG. 2 a section along the line A—A in FIG. 1, FIG. 3 a view of a hook receptacle according to FIG. 2 in a second embodiment, FIG. 4 a section along the line B—B in FIG. 3 and FIG. 5 a representation according to FIGS. 2 and 3 of a hook receptacle in a third embodiment.

DETAILED DESCRIPTION OF THE INVENTION

Figure 1:
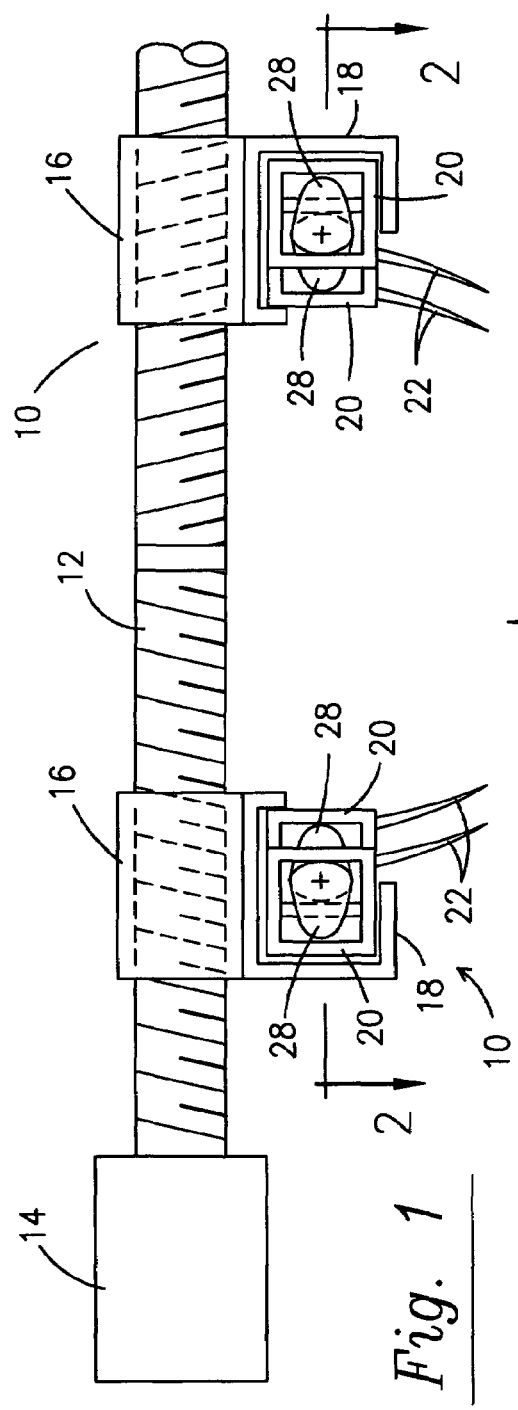

In FIG. 1 an instrument for stretching the tissue of the skin, a so-called skin distractor, is shown. The basic construction of such a skin distractor as such as known and described for example in U.S. Pat. No. 5,486,196 or DE 44 44 130 A1. The skin distractor comprises two jaws 10, which can be advanced towards each other using suitable adjusting means. The jaws 10 and the adjusting means are only schematically indicated in FIG. 1. The adjusting means could comprise for example a threaded spindle 12, which is driven via a drive 14. The drive 14 could be a manually operable knob or an automated motor drive. The jaws 10 are in this case seated via threaded boxes 16 on the threaded spindle 12. The threaded boxes 16 exhibit counter-rotating threads, so that during a rotation of the threaded spindle 12 the jaws 10 move towards each other, while in the case of the counter-rotation of the threaded spindle 12 they move apart. The jaws 10, their control of guidance and their adjustment means can be constructed in various known manner and as such do not comprise part of the invention.

The jaws 10 respectively exhibit one hook receptacle 18, in which hook module 20 can be seated. The hook receptacle 10 and the hook module 20 are so designed, that at least two hook modules 20 can be seated next to each other in the hook receptacle 18. In the shown embodiment respectively five hook modules 20 are seated in a hook receptacle 18. The hook receptacle 18 is provided on the jaws 10 in such a manner, that the hook modules 20 seated in the hook receptacle 18 are arranged side-by-side in a row, whereby this row runs perpendicular to the adjustment path of the jaws 10, that is, in the illustrated embodiment according to FIG. 1 transverse to the threaded spindle 12. The hook module 20 carries hooks 22. Each hook module 20 preferably carries only one hook 22, however in certain cases the hook module 20 could exhibit several hooks 22. The hooks 22 are stuck into the skin and form pull means anchorable in the skin at points. If these jaws 10 are advanced towards each other following the sticking in of the hooks into the skin, then thereby a pull force is introduced into the skin at points via the hooks 22, as necessary for stimulation of tissue stretching.

In the illustrated embodiments the hook receptacles 18 are in the form of hollow forms, preferably hollow quadratic shapes, in which the hook modules 20 can be inserted. The hook modules 20 exhibit a cross-section adapted to the quadric hollow shape of the hook receptacle 18, so that in later described manner there are movable in the hook receptacle 18 perpendicular to the longitudinal axis of the profile, that is in the direction of the pull force or as the case may be in the movement direction of the jaws 10.

Figure 2:
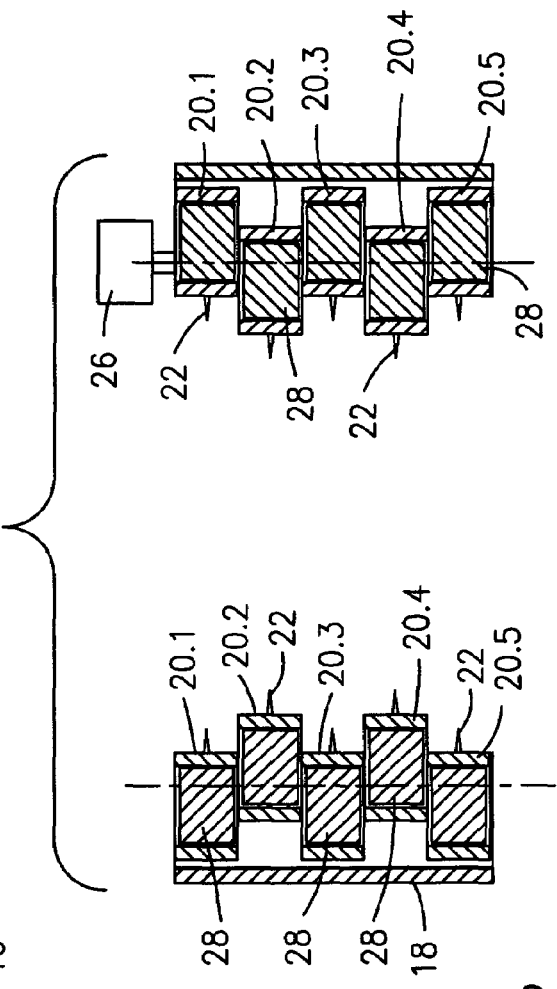

As can be seen particularly from FIGS. 2, 3 and 5, the hook modules 20 are divided into two groups in the hook receptacles 18, whereby the hook modules 20 of the two groups in the hook receptacle 18 alternate. The hook module 20 of the one group, in the illustrative embodiment the hook modules 20.1, 20.3 and 20.5, are thus set off by gaps with respect to the module 20 of the second group, in the illustrated embodiment the hook modules 20.2 and 20.4. The hook modules 20.1, 20.3 and 20.5 and the hook modules 20.2 and 20.4 of the second group are respectively groupwise moveable relative to each other, as shown in FIGS. 2, 3 and 5.

This opposing moveability of the hook modules 20 with the hooks 22 makes possible the following process for stretching the tissue of the skin.

The hooks 22 are stuck into the skin to be stretched. For example, the hooks 22 of the two jaws 10 are stuck into the skin on the oppositely lying edges of a large surface area skin defect or a wound. The jaws 10 are then moved towards each other via the adjusting means 12, 14, in order to bring the wound edges towards each other and to stretch the skin outside of the wound edges. In accordance with the invention the drive of the jaws 10 occurs in such a manner, that a high pull force is exercised on the skin via the hooks 22. The pull force essentially may not exceed the tear resistance of the skin, which is approximately 15 N/mm$^2$ since in this case the hooks 22 would be torn from the skin. Since the hook module 20 of the one group is advanced in the pull direction, this high pull force is introduced into the skin essentially only via the hooks 22 of the advanced hook module, that is, in the representation according to FIGS. 2 and 5, by the hook modules 20.1, 20.3 and 20.5, and in the representation according to FIG. 3 by the hook modules 20.2 and 20.4. The hooks 22 arranged side-by-side in the hook receptacle 18 exhibit a separation from each other of approximately 5–15 mm. Thereby, the skin is tensioned and stretched by the group of advanced hook modules over the entire breadth of the hook receptacle 18, while the retracted hook modules 20.2 and 20.4 lying between the advanced hook modules 20.1, 20.3 and 20.5 exercise upon the skin via their hooks 22 only a low pull force or even no pull force.

The high pull force, which is introduced via the advanced hooks 22 of the hook module 20.1, 20.3 and 20.5 (FIG. 2) in the skin has the consequence, that on the pressure side of the hooks 22 a compression pressure is exercised on the skin tissue, which exceeds the critical closure pressure of the venous capillary system of the skin tissue which lies at approximately 20–40 mm/Hg. This pull load of the tissue is thus maintained only for a period of time, which lies clearly below the ischemia tolerance of the skin tissue of approximately 7 hours. This time period lies between several minutes and several few hours. A shorter period of time of approximately minutes, for example less than 30 minutes, is possible in particular with an automatic controlled drive. A longer period of time of approximately 1–3 hours is preferred in the case of the employment of personnel for a manual adjustment. Following this time period the hook modules 20 of the two groups are displaced relative to each other, so that now the hook module 20 of the first group and the second group exchange their position. The hook modules 20.1, 20.3 and 20.5 of the first group move out of the position shown in FIG. 2 towards the back and the hook modules 20.2 and 20.4 of the second group are then advanced towards the front so that the positions shown in FIG. 3 are assumed. Now the high pull load, which is caused by the adjustment of the jaws 10, is introduced into the skin by the hooks 22 of the second group. The hooks 22 of the retracted hook module 20 are relaxed and exercise upon the skin tissue lying on their pressure side little or no compression pressure. This compression pressure lies significantly below the critical closure pressure of the venous capillary system of the tissue, so that blood perfusion in the tissue on the pressure side of the hooks 22 occurs and a rapid restoration of blood flow through this tissue occurs.

By the position exchange of the hook modules 20.1, 20.3 and 20.5 of the first group and the hook modules 20.2 and 20.4 of the second group occurring over set period of time it is possible to carry out the skin stretching over a long treatment duration of hours and days, wherein the maximal pull load can be exercised on the tissue continuously over the entire breadth of the hook receptacles 18. The spot or point loading alternates thereby however in regular time intervals between the hooks 22 of the first group and the hooks 22 of the second group, so that despite the high pull load a tissue damage due to low blood flow does not occur.

The alternating displacement of the hook modules 20 of the first and second groups can be accomplished in various ways.

In the embodiment according to FIGS. 1 and 2 the hook modules 20 exhibit the shape of a cubic hollow body. An adjusting shaft 24 transitions through the hollow body of the hook module 20, which exhibits on its one end an adjustment drive 26. The adjustment drive is only shown schematically in FIG. 2. This adjustment drive 26 could be a rotation knob for a manual adjustment or an automatically controlled motorized drive for an automatic adjustment. On the adjustment shaft 24 are seated adjustment cams 28, wherein for each hook module 20 an associated adjustment cam 28 is provided. The adjustment cams 28 are preferably in the form of so-called same-thickness and lie with their front and their rear profile inner surface against the hook module 20. The adjustment cams 28 associated with the hook modules 20.1, 20.3 and 20.5 of the first group are displaced at an angle of 180° with respect to the adjustment cams 28 associated with the second group of hook modules 20.2 and 20.4, as can be clearly seen from FIGS. 1 and 2.

A rotation of the adjustment shafts 24 by 180° results in this embodiment in an exchange of the positions of the hook modules 20.1, 20.3 and 20.5 of the first group with the hook modules 20.2 and 20.4 of the second group. Since the adjustment cams 28 lie against the front and the rear inner wall surfaces of the hook modules 20, the hook modules 20 are positively moved both in the forward movement as well as in the retraction movement by the adjustment cams 28. The relaxation of the hooks 22 of the retracted hook module 20 occurs thus by force and independent of the elastic return spring force exercised by the skin upon these hooks.

In FIGS. 3 and 4 an alternative embodiment is shown.

In this embodiment the adjustment shaft 24 runs behind the hook modules 20. On the adjustment shaft 24 are seated adjustment cams 28, which are respectively associated with the individual hook modules 20. Therein the adjustment cams 28 which are associated with the hook modules 20.1, 20.3 and 20.5 of the first group are set off with respect to the adjustment cams 28 which are associated with the hook modules 20.2 and 20.4 of the second group by 90° on the adjustment shaft 24, as can be seen in FIG. 4. In the representation according to FIGS. 3 and 4 the adjustment cams 28 of the hook modules 20.2 and 20.4 are in engagement and push these hook modules in the advanced position. The adjustment cams 28 of the hook modules 20.1, 20.3 and 20.5 are in comparison thereto pivoted back, so that they release the associated hook modules. Upon a rotation of the adjustment shaft 24 by 90° (in FIG. 4 in the counter-clock sense) the adjustment cams 28 of the other group come into engagement and push the associated hook modules 20.1, 20.3 and 20.5 in the active position while the adjustment cams 28 of the hook modules 20.2 and 20.4 are pivoted back and the associated hook modules are released.

In this embodiment the hook modules 20 are positively moved in the advanced position and held there by the adjustment cams 28. The inactive hook modules 20 are only released by the associated adjustment cams 28, so that these are no longer supported. The hook module 20 moves back in this embodiment on the basis of the elastic return spring force of the skin acting upon the hooks 22. The relaxed hook modules move back under the elasticity effect of the skin to the point that their hooks 22 no longer exercise any significant force on the skin. Thereby the compression force exercised by the relaxed hook modules 20 on the pressure side of the hooks 22 upon the skin tissue falls to practically zero.

In FIG. 5 a further embodiment is shown, in which the individual hook modules 20 are respectively associated with individual adjustment means 30. These adjustment means can be of any construction, for example as adjustment screws or as shown in FIG. 5 a pneumatic cylinder-piston adjustment means. Since the hook modules 20 are respectively individually adjustable via their associated adjustment means 30, in this embodiment a flexible distribution of the pull forces over the breadth of the hook receptacles 18 is possible. In addition such an adjustment is suitable in particular for automation. If the adjustment means 30 additionally engage via an elastic pad or cushion 32 against the hook modules 20, as indicated in FIG. 5, then the hook modules 20 can with their respective hooks 22 adapt to and equalize different skin tensions.

In all embodiments of the invention the pull force acting to stretch the tissue is produced by the movement of the jaws 10. This pull force is introduced constantly in the tissue, in particular also in the case of a long time stretching. The introduction of the pull force into the tissue is however over time periodically alternatingly distributed over various hooks. The hooks are thereby relaxed in regular time intervals, so that in the pressure areas the tissue perfusion is completely restored and no necrosis occurs.

REFERENCE NUMBER LIST

10 Jaws
12 Threaded spindle
14 Drive
16 Threaded box
18 Hook receptacle
20 Hook module
22 Hooks
24 Adjustment shaft
26 Adjustment drive
28 Adjustment cam
30 Adjustment means
32 Pad

The invention claimed is:
1. A process for stretching tissue, comprising the steps of:
anchoring at least two pull means to a skin tissue at opposing locations of a skin wound, each pull means anchoring to at least two points in the skin, exercising a pull force upon the skin at the at least two points of anchoring of the at least two pull means by pulling the at least two pull means towards each other, alternating the pull force over time at each point of anchoring between at least a first and a second value, wherein the first value pull force is applied to a portion of the at least two points at which the pull means is anchored, and at the same time, the second value pull force is applied to another portion of the at least two points at which the pull means is anchored, wherein the first value is below the threshold at which the pull means would be torn out, and above a threshold value which causes ischemia in the skin tissue on the pressure side of the pull means, wherein the second value lies below the threshold value which causes ischemia in the skin tissue on the pressure side of the pull means, wherein the pull force is maintained at the first value respectively for a period of time, which lies below the ischemia tolerance duration of the skin tissue and wherein the pull force is maintained at the second value respectively for a period of time which makes possible a complete reperfusion of the skin tissue.

2. A process according to claim 1, wherein the pull force is maintained at the first value respectively for more than a half hour.

3. A process according to claim 2, wherein the pull force is maintained at the second value respectively for a time period of 0.5 to 5 minutes.

4. A process according to claim 1, wherein the pull means are arranged side-by-side in a row transverse to the direction of the pull force and in this row alternatingly exercise the pull force with the first and the second value.

5. A process according to claim 1, wherein the pull means which respectively exercise the pull force with the first value and the pull means which respectively exercise the pull force with the second value oppose each other in the direction of the pull force and alternate their positions.

6. A process according to claim 5, wherein the respective pull means exercising the pull force with the second value are relaxed and exercise no pull force on the skin.

7. A process according to claim 1, wherein the pull force is maintained at the first value respectively for a period of time of less than 7 hours.

8. A process according to claim 7, wherein the pull force is maintained at the second value respectively for a time period of 0.5 to 5 minutes.

9. A process for closing a wound, comprising the steps of:

providing an instrument for stretching tissue of the skin, the instrument having jaws, with hook modules introduced in hook receptacles of the jaws, which respectively carry at least one hook, wherein the hooks are anchored to at least two points in the skin on opposite sides of the wound and are moveable towards each other in order to introduce a pull force into the skin via the hooks stuck in the skin, anchoring the hooks to at least two points in the skin, exercising a first pull force on a first portion of the hooks anchored to the skin, exercising a second pull force on a second portion of the hooks anchored to the skin at the same time during which the first pull force is exercised on the first portion of the hooks, alternating application of the first pull force and the second pull force to the first portion and second portion of hooks, wherein the value of the first pull force is below the threshold at which the pull means would be torn out, and above a threshold value which causes ischemia in the skin tissue on the pressure side of the pull means, wherein the value of the second pull force lies below the threshold value which causes ischemia in the skin tissue on the pressure side of the pull means, wherein the first pull force is maintained for a period of time, which lies below the ischemia tolerance duration of the skin tissue and wherein the second pull force is maintained for a period of time which makes possible a complete reperfusion of the skin tissue.

10. A process for closing a wound, comprising the steps of:

providing a skin stretching instrument with opposing skin anchoring devices, each skin anchoring device having a series of first skin anchoring structures and a series of second skin anchoring structures;

anchoring the series of first and second skin anchoring structures of the opposing skin anchoring devices to points of the skin;

alternating application of a skin stretching force, between the opposing skin anchoring devices and which is applied at the series of first skin anchoring structures and the series of second skin anchoring structures, with application of a skin reperfusion force, between the opposing skin anchoring devices and which is applied at the series of first skin anchoring structures and the series of second skin anchoring structures;

wherein the alternating application of the skin stretching force and the skin reperfusion force is such that the skin stretching force is applied to the series of first skin anchoring structures when the skin reperfusion force is applied to the series of second skin anchoring structures and the skin stretching force is applied to the series of second skin anchoring structures when the skin reperfusion force is applied to the series of first skin anchoring structures; and wherein the reperfusion force allows reperfusion of the skin tissue.

* * * * *